United States Patent [19]
Harris

[11] Patent Number: 4,744,370
[45] Date of Patent: May 17, 1988

[54] LEAD ASSEMBLY WITH SELECTABLE ELECTRODE CONNECTION

[75] Inventor: Donald L. Harris, Key Largo, Fla.

[73] Assignee: Cordis Leads, Inc., Miami, Fla.

[21] Appl. No.: 42,677

[22] Filed: Apr. 27, 1987

[51] Int. Cl.[4] .......................... A61N 1/05; H01R 17/18

[52] U.S. Cl. .......................... 128/786; 439/668; 439/669

[58] Field of Search .............. 128/786, 781, 785, 642, 128/419 C, 419 D, 784; 439/668, 669, 909

[56] References Cited

U.S. PATENT DOCUMENTS

| | | | |
|---|---|---|---|
| 3,291,926 | 12/1966 | Nelson | 439/669 |
| 3,546,657 | 12/1970 | Cook | 439/668 |
| 4,379,462 | 4/1983 | Borkan et al. | 128/786 |
| 4,628,934 | 12/1986 | Pohndorf et al. | 128/786 |
| 4,630,611 | 12/1986 | King | 128/642 |
| 4,644,960 | 2/1987 | Johans | 128/786 |
| 4,667,686 | 5/1987 | Peer-Travarton | 128/419 P |
| 4,672,979 | 6/1987 | Pohndorf | 128/419 P |

*Primary Examiner*—Eugene F. Desmond
*Assistant Examiner*—Paula A. Austin
*Attorney, Agent, or Firm*—Henry W. Collins; Thomas R. Vigil

[57] ABSTRACT

The multi-conductor lead assembly comprises a first lead, a second lead and a connector assembly for connecting the leads together. The first lead includes a lead body having a distal end portion with a plurality of electrodes thereon, a proximal end portion with a plurality of sleeve electrodes thereon and a plurality of insulated wire conductors within the lead body and electrically connecting the electrodes on the distal end portion with the sleeve electrodes on the proximal end portion. The second lead includes a lead body with a proximal end, a proximal end portion, a distal end and a distal end portion, and one wire conductor therein. The connector assembly includes a body, the distal end portion of the second lead being received in the body, a connector clip adapted to make electrical contact with a selected one of the plurality of sleeve electrodes on the first lead, an electrical connection between the wire conductor in the second lead and the connector clip, and a closure sleeve for insulating the connection between the connector clip and a selected sleeve electrode.

13 Claims, 4 Drawing Sheets

LEAD ASSEMBLY WITH SELECTABLE ELECTRODE CONNECTION

BACKGROUND OF THE INVENTION

1. Field of the Invention

The present invention relates to a multi-conductor lead assembly comprising a first lead, a second lead and a connector assembly for connecting the proximal end portion of the first lead to the distal end portion of the second lead. More specifically, the invention relates to the connector assembly which provides a simple and effective structure for connecting a conductor in the second lead to one of several sleeve electrodes on the proximal end of the first lead in a sealed manner whereby the connector assembly can be inserted in body tissue after the distal end of the first lead with ring electrodes thereon has been implanted in body tissue, electrical tests first have been made, by means of electrical connections to the sleeve electrodes on the proximal end of the first sleeve, on the sensitivity of the implanted ring electrodes and a connection is made from a selected ring electrode on the distal end of the first lead to the conductor in the second lead.

2. Description of the Prior Art

Heretofore, it has been desirable, in the field of multi-electrode leads which are inserted into the epidural space within the spine and adjacent the spinal cord, to be able to determine which of a number, such as, for example, four, electrodes implanted in the spine are in good conductive contact with the spinal cord. In this respect, it is desirable to be able to test and determine which of the distal electrodes has the best conductive contact with the spinal cord.

One technique which has been proposed for achieving this result is to provide a cathode electrode assembly having four equally spaced in line electrodes along the exterior of a sheath at the distal end of the catheter which are connected to proximal terminals at the proximal end by individually insulated strands of steel wire conductor.

A wire is connected to and extends from each of the proximal terminals to an external terminal each of which is adapted to extend out of body tissue for cutaneous testing during a trial period of stimulation. The wires are cut adjacent the proximal terminals and removed prior to permanent implantation of the multi-conductor lead assembly and before the proximal terminals at the proximal end of the catheter are connected to an implanted stimulator.

Such an assembly is disclosed in the Borkan et al U.S. Pat. No. 4,379,462.

As will be described in greater detail hereinafter, the multi-conductor lead assembly of the present invention, instead of having external terminals which are cut away from a lead, includes two leads, a first lead which has distal electrodes adapted to be implanted within a spine, a second lead with having a wire conductor therein and a proximal terminal assembly including a terminal pin adapted to be inserted into a neural stimulator, and a connector assembly at the distal end of the second lead into which the proximal end of the first lead is adapted to be inserted after testing is performed, such as with alligator clips connected to sleeve electrodes on the proximal end portion of the first lead when it is withdrawn from the tissue for testing purposes. After the testing, the proximal end of the first lead is inserted into the connector assembly and a clip connector at the distal end of an insulated wire conductor connected to the wire conductor in the second lead is connected to a selected one of the sleeve electrodes on the proximal end of the first lead. Then the connector assembly is sealed and implanted in body tissue and the proximal end of the wire conductor in the second lead is connected to an implanted or external neural stimulator.

SUMMARY OF THE INVENTION

According to the present invention there is provided a multi-conductor lead assembly comprising:

a first lead including a lead body having a distal end portion with a plurality of electrodes thereon, a proximal end portion with a plurality of sleeve electrodes thereon and a plurality of insulated wire conductors within the lead body and electrically connecting the electrodes on said distal end portion with the sleeve electrodes on the proximal end portion;

a second lead including a lead body having a proximal end, a proximal end portion, a distal end and a distal end portion, and an insulated wire conductor therein having a proximal end and a distal end;

a terminal assembly including a terminal pin connected to the proximal end of the wire conductor in the second lead; and a connector assembly including a body, the distal end portion of the second lead being received in the body, a flexible insulated wire conductor having a proximal end in the body and electrically connected to the distal end of the wire conductor in the second lead and a distal end, a connector clip connected to the distal end of the flexible insulated wire conductor and adapted to make electrical contact with a selected one of the plurality of sleeve electrodes on the first lead, and means for insulating the connection between the connector clip and a selected one of the sleeve electrodes.

DESCRIPTION OF THE PREFERRED EMBODIMENT

Figures 1, 2:
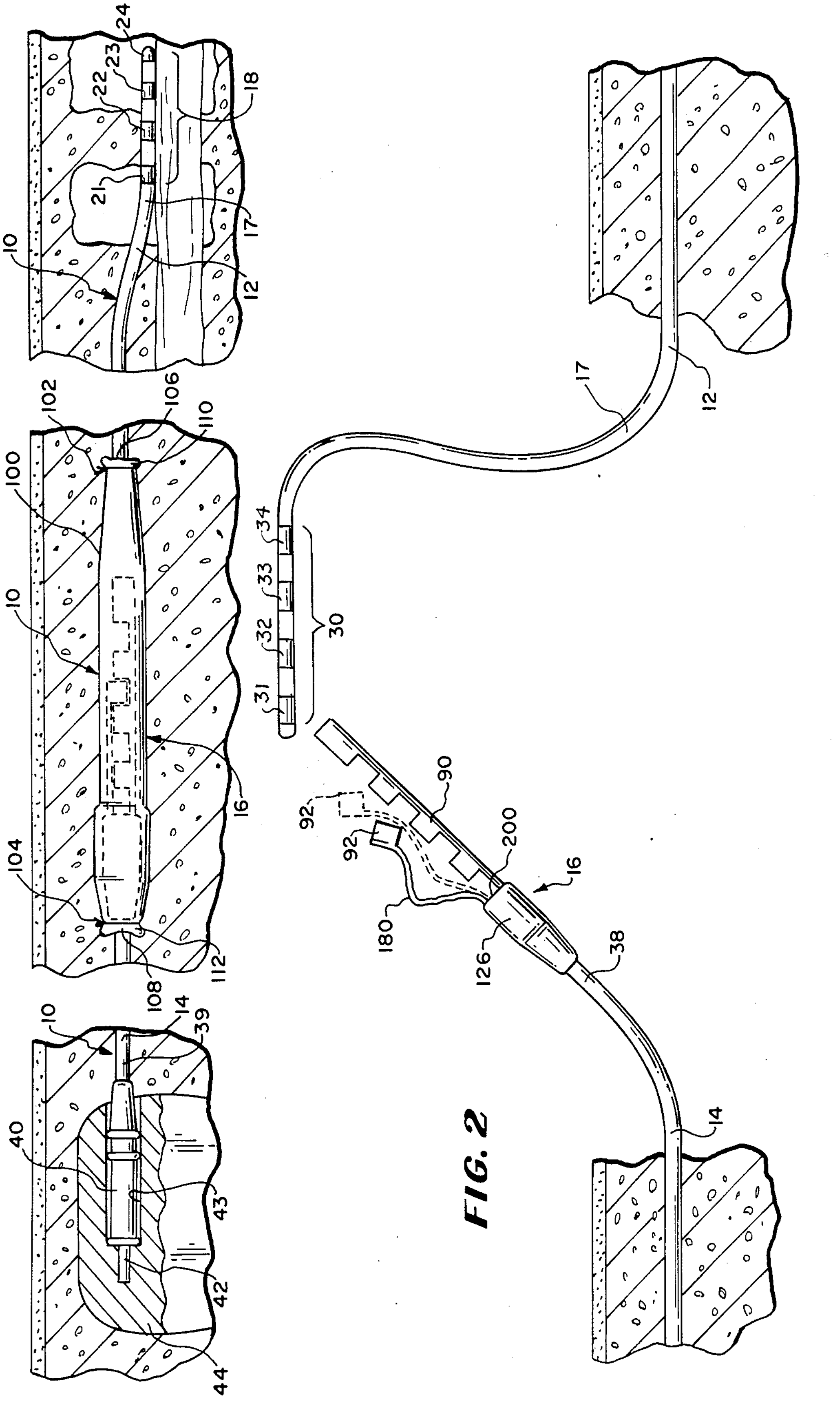
FIG. 1 is a longitudinal plan view with portions broken away of the multi-conductor lead assembly of the present invention and shows a proximal end of a first lead of the assembly inserted in the epidural space of the spine, a proximal end of a second lead extending into an implanted neural stimulator and a connector assembly in which the proximal end of the first lead and the distal end of the second lead are connected together.
FIG. 2 is a longitudinal plan view of the proximal end portion of the first lead and the connector assembly withdrawn from tissue.

In FIG. 1 there is illustrated a multi-conductor lead assembly 10 constructed according to the teachings of the present invention. The assembly 10 includes a first distal lead 12, a second proximal lead 14, and a connector assembly 16 connecting the two leads 12 and 14 together.

FIG. 1 shows the connector assembly 16 of the present invention in its assembled sealed state mounted within body tissue.

The first lead 12 includes a lead body 17 having a distal end portion 18 having four ring electrodes 21–24 (or three ring electrodes 21–23 and one tip electrode 24) (FIG. 1) thereon which are positioned within the epidural space of the spine so that at least one of the ring electrodes 21–24 is in a position to supply electrical current signals to nerve tissue for the purpose of interfering with, and blocking, pain signals. The electrical current path can be between one ring electrode 21–24 and an anode connected to the body remotely from the position of the ring electrodes 21–24 or between any two of the ring electrodes 21 and 24 when two spring connector clips (92 in FIG. 2) are provided.

A proximal end portion 30 (FIG. 2) of the first lead 12 hidden from view in FIG. 1 has four sleeve electrodes 31–34 (FIG. 2) which are received in the connector assembly 16. The connector assembly 16 is mounted on a distal end portion 38 of the second lead 14.

The second lead 14 has a proximal end 39 mounting a terminal assembly 40 which has a terminal pin 42. The terminal assembly 40 is received in a socket 43 in an implanted neural stimulator 44 for electrically connecting the terminal pin 42 to electrical circuitry within the neural stimulator 44.

As will be described in greater detail hereinafter, once it is determined, such as by testing, which one or ones of the ring electrodes 21–24 in the distal end portion 18 of the first lead 12 is best positioned for supplying stimulating current to nerve tissue, a selected ring electrode 21, 22, 23, or 24 (identified such as by electrical conductivity testing) is connected through the connector assembly 16 to the terminal pin 42.

In use, the distal end portion 18 of the first lead 16 is inserted into the epidural space in the spine of a body. Then, the proximal end portion 30 of the first lead 12 is brought out of the body, as shown in FIG. 2, so that tests can be made by making connections, such as with alligator clips (not shown) between a conductivity sensor (not shown) and the sleeve electrodes 31–34 to determine the sensitivity or effectiveness of contact of each ring electrode 21–24 of the first lead 12 to the spinal cord. In this way, the ring electrode 21–24 which will be connected via connector assembly 16 to the terminal pin 42 is determined.

Then the proximal end 30 of the first lead 12 is inserted on a rigid leg 90 (FIG. 4) of the connector assembly 16 and a spring connector clip 92 is snapped over the sleeve electrode 32, 32, 33 or 34 connected to the selected ring electrode 21, 22, 23 or 24.

Figure 3:
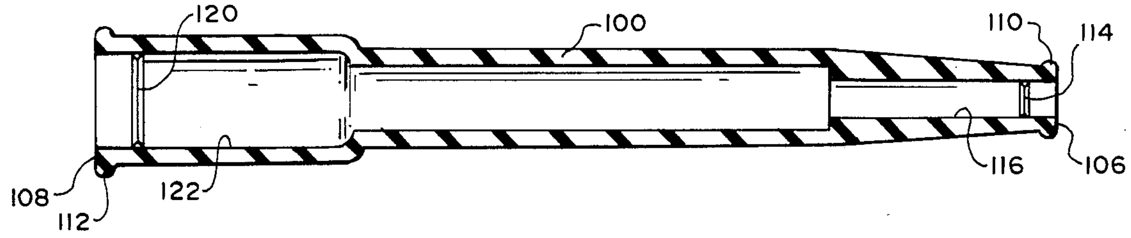
FIG. 3 is a longitudinal sectional view of a closure sleeve which is received on the proximal end of the first lead prior to the insertion of the proximal end of the first lead onto a leg of the connector assembly and a clip connector is connected to a selected sleeve electrode after which the closure sleeve is moved over the connector assembly for facilitating a sealed closure over and about the leg and connector clip by the tying of sutures around and adjacent each end of the closure sleeve.

Of course, before this is done a closure sleeve 100 (FIG. 3) is inserted over the proximal end portion 30 of the first lead 12 and far enough up on the lead 12 so that the proximal end portion 30 of the first lead 12 can be inserted on the leg 90 of the connector assembly 16. Then, after the clip 92 is connected to one of the sleeve electrodes 31–34, the closure sleeve 100 is slid back over the connector assembly 16 and sutures 102 and 104 (FIG. 1) are tied around each end 106 and 108 of the sleeve 100 to fix the closure sleeve 100 over the connector assembly 16 and to seal the connections in the connector assembly 16 from body fluids. This is assisted by providing a bead 110 at the end 106 of the sleeve 100 and a bead 112 at the end 108 of the sleeve 100 for keeping each suture 102, 104 (FIG. 1) on the sleeve 100 so it will not come off the respective end of the sleeve 100.

Additionally, an annular rib 114 can be provided within a lumen 116 of the sleeve 100 adjacent the end 106 which is received over the first lead 12 and a similar annular rib 120 can be provided in a larger lumen 122 of the sleeve 100 adjacent the end 108 of the sleeve 100 which is received over a cylindrical body 126 (FIG. 5) of the connector assembly 16 for providing an internal seal between the interior of the sleeve and the body 126 and the first lead 12.

Figure 5:
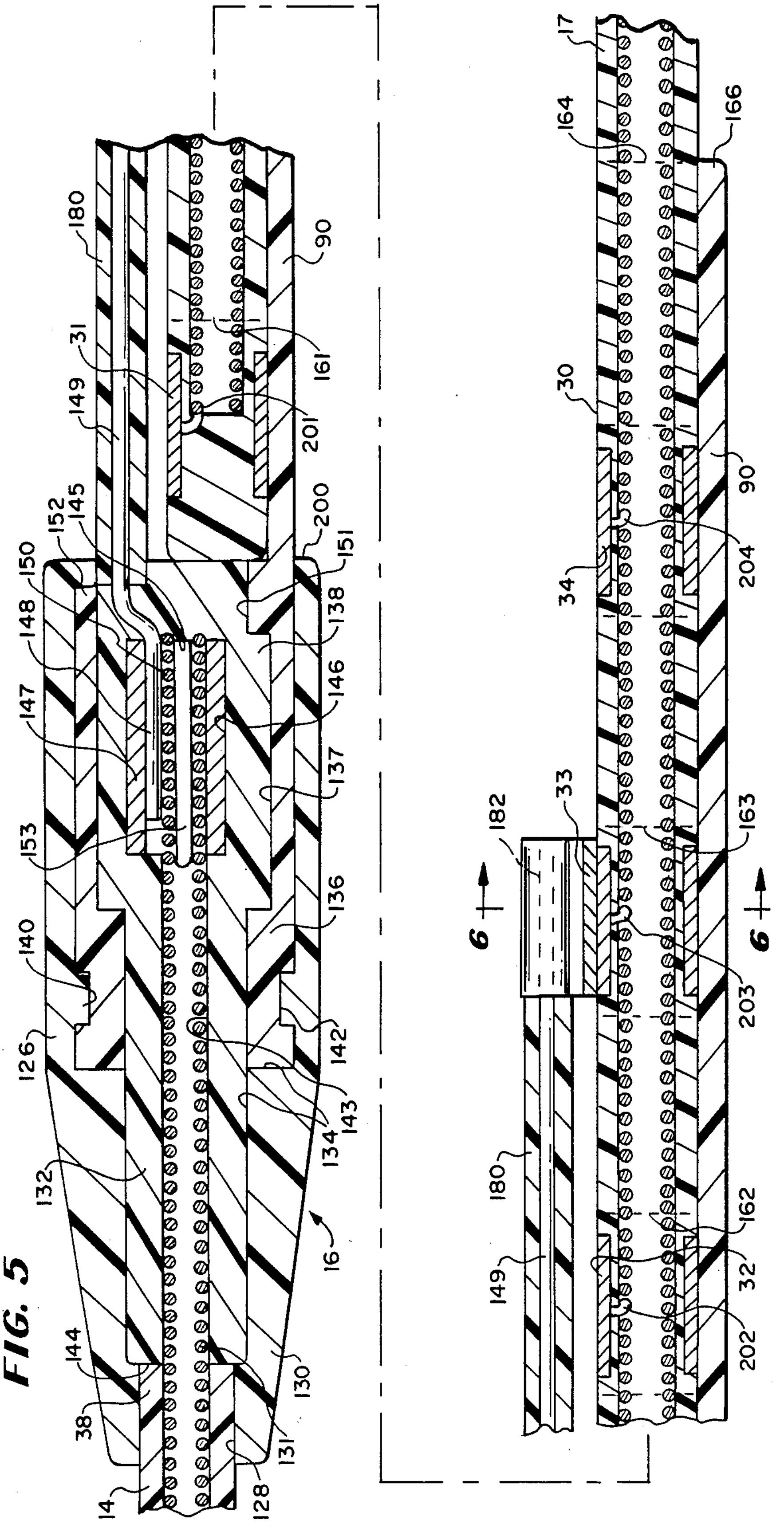
FIG. 5 on the third sheet of drawings is a longitudinal sectional view through the connector assembly shown in FIG. 4 after the proximal end of the first lead is placed on a rigid leg of the connector assembly and a connector clip at the distal end of a flexible insulated wire conductor is fixed over and on a sleeve electrode on the proximal end portion of the first lead.

As best shown in FIG. 5, the connector assembly 16 of the present invention has the distal end portion 38 of the second lead 14 received in a bore 128 in a tapered proximal end portion 130 of the body 126. A coiled wire conductor 131 in the second lead 14 extends from the proximal end portion 38 where it is connected to the terminal pin into a finger 132 received in a stepped cavity 134 in the body 126.

Within the stepped cavity 134 in the body portion 126, is positioned a cylindrical sleeve 136 made of a more rigid plastic material, such as a thermoplastic material. This sleeve 136 has an at least partially annular hollow 137 which receives an at least partially annular boss 138 of the finger 132 thereby to prevent relative longitudinal movement between the finger 132 and the cylindrical sleeve 136.

Also, as shown in FIG. 5, the body portion 126 has, within the cavity 134, an annular rib 140 which is received in an annular groove 142 on the outer surface of the cylindrical sleeve 136 to prevent relative longitudinal movement between the body 126 and the cylindrical sleeve 136.

The finger 132 is made of a flexible elastomeric material and has a bore 143 opening onto a proximal end 144 of the finger 132 and extending to an internal end wall 145. An inner end portion 146 of the bore 143 is larger in diameter and has a metal sleeve 147 pressed into the inner end portion 146. The coiled conductor 131 extends into the bore 143 and into the inner end portion 146 where a proximal end 148 of a wire conductor 149 is positioned between the sleeve 147 and a coiled end portion 150 of the wire conductor 131. Preferably, the sleeve 147, the wire end portion 148 and the coiled wire end portion 150 are soldered together. Alternatively, a pin 153 can be inserted as shown in FIG. 5 into the coiled end portion 150 and the entire assembly can be crimped.

The rigid leg 90 is integral with and extends axially outwardly from the cylindrical sleeve 136 adjacent a partially annular rib 151 at a distal end 152 of the sleeve 136. The rigid leg 90 is also made of a hard, stiff, rigid, thermoplastic material.

Figure 6:
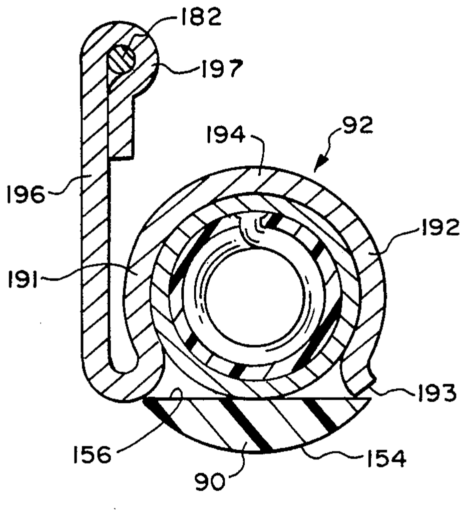
FIG. 6 on the second sheet of drawings is a sectional view through the connector assembly shown in FIG. 5 and is taken along line 6-6 of FIG. 5.
Figure 7:
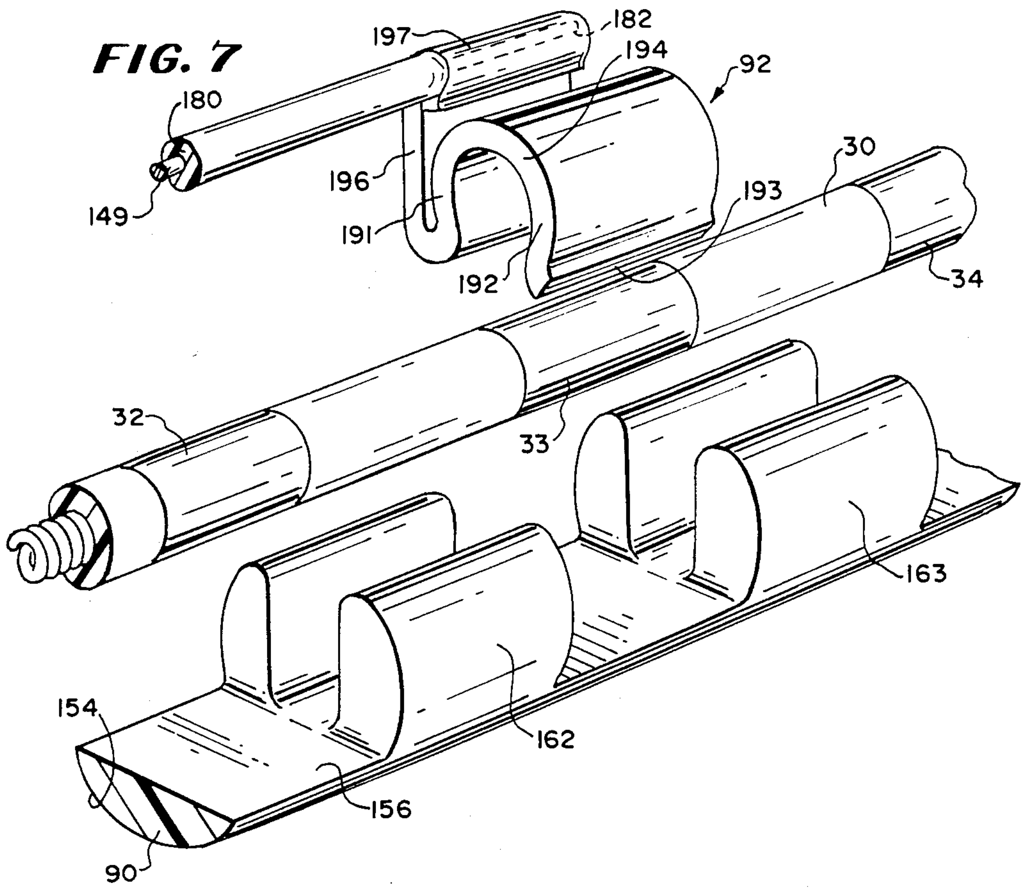
FIG. 7 is an enlarged perspective view of a section of the proximal end portion of the first lead above two saddle formations on the rigid leg and below the connector clip at the distal end of a flexible insulated wire conductors of the connector assembly.

As best shown in FIGS. 6 and 7, the rigid leg 90 has a partially cylindrical outer surface 154 and a flat inner or upper surface 156 with four saddle formations 161–164 extending upwardly from the flat surface 156. The saddle formations 161, 162, and 163 are adapted to receive segments of the proximal end portion 30 of the first lead 12 between the spaced apart sleeve electrodes 31–34 thereon.

Figure 8:
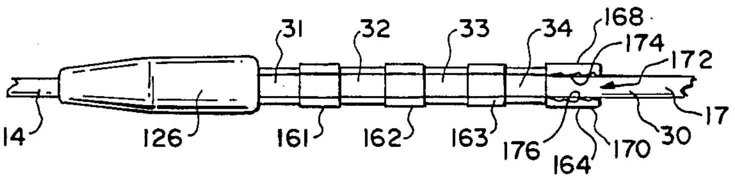
FIG. 8 is a longitudinal plan view taken along line 8—8 of FIG. 5 and shows a gripping formation on the distal end portion of the rigid leg of the connector assembly for gripping the proximal end portion of the first lead.

The distal saddle formation 164, located at a distal end 166 of the rigid leg 90, includes a first jaw 168 (FIG. 8) and a second jaw 170 (FIG. 8) separated by a slot 172 (FIG. 8). The sides of the jaws 168, 170, facing each other on each side of the slot 172 have teeth 174, 176 (FIG. 8) thereon for gripping the proximal end portion 30 of the first lead 12, just distal of the proximal end portion 30 thereof, to assist in holding the proximal end portion 30 of the first lead 12 on the leg 90 of the connector assembly 16.

Figure 4:
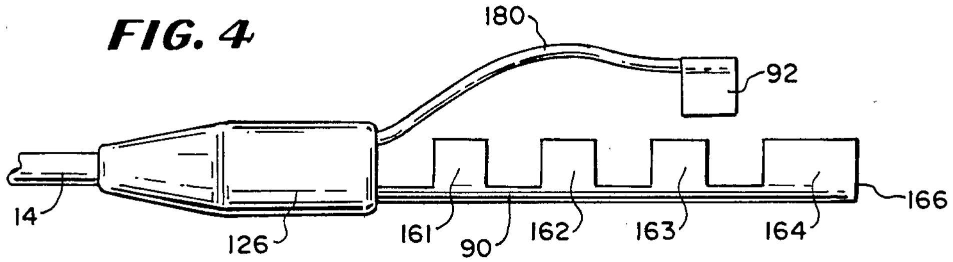
FIG. 4 is a longitudinal side view of the connector assembly at the distal end of the second lead.

The wire conductor 149 extends from its proximal end 148 into and through a flexible elastomeric sheath 180 which can be flexed and raised above the stiff rigid leg 90, as shown in FIGS. 2 and 4 to a distal end 182 which is fixed to the spring connector clip 92.

As shown in FIGS. 6 and 7, the connector clip 92 includes a first leg portion 191, a second leg portion 192 having a free edge 193, and a bight portion 194. The first leg portion 191 has a connector leaf or blade 196 integral therewith and extending upwardly generally parallel to the first and second leg portions 191 and 192 to a rounded curled over or bent end portion 197. The bare distal end 182 of the wire conductor 149 is received in the curled over or bent end portion 197 of the leaf 196 which is crimped over the uninsulated end 182 to make a mechanical and electrical connection therewith.

The inside width of the U-shaped connector clip 92 is less than the outer diameter of each of the sleeve electrodes 31–34 so that an interference friction fit is made between the clip 92 and a selected one of the sleeve electrodes 31–34 when the clip 92 is brought down over the proximal end portion 30 of the first lead 12 and against the rigid leg 90.

This is done, of course, after the sleeve electrodes 31–34 are aligned and in registry with the spaces between a distal end 200 of the body 126 and the saddle formations 161, 162, 163 and 164 on the leg 90.

As shown schematically in FIG. 5, the first lead 12 has four insulated coiled wire conductors 201–204 therein.

A wire conductor 201 in the proximal end portion 30 of the first lead 12 has an uninsulated end portion that is brought out of the lead body 17 to make connection with the sleeve electrode 31. Likewise, the proximal end portions of wire conductors 202, 203, 204 are connected to sleeve electrodes 32, 33 and 34.

In use, as described above, after the distal end portion 18 of the first lead 12 is inserted in the epidural space within the spine of a body, the sensitivity or conductive path between each of the ring electrodes 21, 22, 23 and 24 and adjacent nerve tissues is determined by performing conductivity tests, such as by making selective connections to the sleeve electrodes 31, 32, 33 and 34 on the proximal end portion 30 of the first lead 12 which is withdrawn from the body for this purpose.

Once the sensitivity or threshold level of each of the ring electrodes 21, 22, 23 and 24 is determined, the closure sleeve 100 is inserted over the proximal end portion 30 of the first lead 12. Then the proximal end portion 30 of the first lead 12 is placed on the rigid leg 90 with the sleeve electrodes 31–34 in the spaces between the distal end 200 of the cylindrical sleeve 136 and the saddle formations 161–164. Then the connector clip 92 is squeezed over a selected one of the sleeve electrodes 31, 32, 33 and 34.

Then the closure sleeve 100 is moved over the leg 90 and the body 126 and the sutures 102 and 104 are tied in place to seal the closure sleeve 100 about the body 26 and legs 91 and 92 of the connector assembly 16 and particularly about the first and second legs 90 with the proximal end portion 30 of the first lead 12 thereon.

The sutures 102 and 104 are tied about the respective ends 106 and 108 of the closure sleeve 100 to seal the connector assembly 16, after which the connector assembly 16 is implanted within body tissue as shown in FIG. 1.

From the foregoing description, it will be apparent that the multi-conductor neural stimulating assembly 10 of the present invention and particularly the connector assembly 16 thereof have a number of advantages some of which have been described above and others of which are inherent in the invention. In particular, the simple and easy way of connecting the proximal end portion 30 of the first lead 12 to the connector assembly 16 and the sealing of same enables testing of the sensitivity or threshold level of each ring electrode 21, 22, 23 and 24 adjacent nerve tissue in the epidural space within the spine of the body prior to connection of the lead 12 to the lead 14. The stimulating assembly 10 is particularly adapted for relatively permanent implantation after testing has been effected with a temporary lead assembly of the type disclosed and claimed in copending application Ser. No. 042,834, filed on Apr. 27, 1987 for: MULTI-CONDUCTOR LEAD ASSEMBLY FOR TEMPORARY USE.

Additionally from the foregoing description, it will be understood that modifications can be made to the neural stimulating lead assembly 10 of the present invention and the connector assembly 16 thereof without departing from the teachings of the present invention. For example, a second spring clip 92 can be provided as shown in FIG. 2 to provide a bipolar assembly. Accordingly, the scope of the invention is only to be limited as necessitated by the accompanying claims.

I claim:

1. A multi-conductor lead assembly comprising:

a first lead including a lead body having a distal end portion with a plurality of electrodes thereon, a proximal end portion with a plurality of sleeve electrodes thereon and a plurality of insulated wire conductors within the lead body and electrically connecting said electrodes on said distal end portion with said sleeve electrodes on said proximal end portion;

a second lead including a lead body having a proximal end, a proximal end portion, a distal end and a distal end portion, and an insulated wire conductor therein having a proximal end and a distal end;

a terminal assembly including a terminal pin connected to said proximal end of said wire conductor in said second lead; and a connector assembly including a body, said distal end portion of said second lead being received in said body, a flexible insulated wire conductor having a proximal end in said body and electrically connected to said distal end of said wire conductor in said second lead and a distal end, a connector clip connected to said distal end of said flexible insulated wire conductor and adapted to make electrical contact with a selected one of said plurality of sleeve electrodes on said first lead, and means for insulating the connection between said connector clip and a selected one of said sleeve electrodes.

2. The lead assembly of claim 1 including a second flexible insulated wire conductor in said second lead and a second connector clip connected to the distal end of said second insulated wire conductor.

3. The lead assembly of claim 1 wherein said body of said connector assembly includes a stiff rigid leg, said proximal end portion of said first lead being received on said rigid leg.

4. The assembly of claim 3 wherein said connector assembly body includes an annular housing, one end of said rigid leg is received in said annular housing, and said connector assembly further includes a flexible wire conductor encased in a flexible elastomeric sheath and having a distal end connected to said connector clip and a proximal end received in said housing and connected to the distal end of said conductor in said second lead.

5. The lead assembly of claim 4 wherein said distal end portion of said second lead extends into one end of said annular housing, said wire conductor in said distal end portion extending into a proximal end of a finger where it is connected to the proximal end of said flexible wire conductor of said connector assembly.

6. The lead assembly of claim 4 wherein said rigid leg has a U-shaped formation adjacent the distal end thereof, said U-shaped formation being defined by a bight portion and first and second leg portions, said first and second leg portions having means thereon for engaging said proximal end portion of said first lead for preventing longitudinal movement of said first lead relative to said rigid leg.

7. The lead assembly of claim 6 wherein said means for engaging the proximal end of said first lead comprises teeth on the inner surface of each of said leg portions.

8. The assembly of claim 5 wherein said stiff rigid leg has a plurality of generally U-shaped saddle formations, said U-shaped saddle formations on said stiff, rigid leg being adapted to receive segments of said proximal end portion of said lead body located, in the areas between said sleeve electrodes, on said proximal end portion of said first lead.

9. The lead assembly of claim 8 wherein said annular housing is generally tubular, said proximal end portion of said rigid leg received in said annular housing is at least partially annular, and said finger is received in said at least partially annular proximal end of said rigid leg.

10. The lead assembly of claim 8 wherein said insulating means of said connector assembly includes a tubular closure member which is initially received on said first lead and, after said proximal end portion of said first lead is received on said rigid leg and said connector clip is connected to a selected one of said sleeve electrodes, said tubular closure member is moved over said leg and over said annular housing.

11. The lead assembly of claim 10 wherein said insulating means includes tie means tied around each end of said tubular closure member when it is positioned about said body comprising said housing and said rigid leg with said proximal end portion of said first lead positioned on the rigid leg.

12. The lead assembly of claim 11 wherein said tubular closure member has an exterior annular rib at each end to prevent said tie means from coming off of said tubular closure member.

13. The lead assembly of claim 11 wherein said tubular closure member has an internal annular rib adjacent each end thereof for establishing seals with, respectively, said housing and said lead body of said first lead.

* * * * *